United States Patent
Moriarty et al.

[11] Patent Number: 6,045,757
[45] Date of Patent: Apr. 4, 2000

[54] MEMBRANE FILTER PIPETTE TIP

[75] Inventors: Kent G. Moriarty, Pinole; James S. Petrek, Danville; Kenneth Rainin, Piedmont, all of Calif.

[73] Assignee: Rainin Instrument Co., Inc., Emeryville, Calif.

[21] Appl. No.: 08/885,450

[22] Filed: Jun. 30, 1997

[51] Int. Cl.[7] ..................................................... B01L 3/02
[52] U.S. Cl. ............................ 422/100; 422/99; 422/101
[58] Field of Search ............................... 422/58, 68.1, 99, 422/101–104; 436/177, 178, 180; 210/416.1, 483, 496

[56] References Cited

U.S. PATENT DOCUMENTS

| | | | |
|---|---|---|---|
| 4,014,653 | 3/1977 | Gianos et al. . | |
| 4,267,729 | 5/1981 | Eddelman et al. . | |
| 4,297,173 | 10/1981 | Hikuma et al. | 204/1 T |
| 4,999,164 | 3/1991 | Puchinger et al. | 422/100 |
| 5,156,811 | 10/1992 | White | 422/100 |
| 5,364,595 | 11/1994 | Smith | 422/100 |
| 5,437,979 | 8/1995 | Rampal et al. | 435/6 |
| 5,496,523 | 3/1996 | Gazit et al. | 422/100 |
| 5,580,529 | 12/1996 | DeVaughn et al. . | |
| 5,648,271 | 7/1997 | Kempe | 436/178 |
| 5,719,052 | 2/1998 | Ito et al. | 435/287.1 |

*Primary Examiner*—Jan Ludlow
*Attorney, Agent, or Firm*—Robert R. Meads

[57] ABSTRACT

A membrane filter pipette tip comprising a hollow tube having a relatively large open upper end for seating on a lower end of a pipette tip mounting shaft of a pipette device and having a relatively small lower open end for passing fluid into the lower end of the tube upon operation of the pipette device in an aspiration mode. A porous membrane is secured by a porous plug within the tube across an open channel within the tube extending between the open upper and lower ends thereof and having a fluid initiation/penetration pressure which is greater than the maximum vacuum pressure which the pipette device to which the tube is secured is capable of generating.

2 Claims, 3 Drawing Sheets

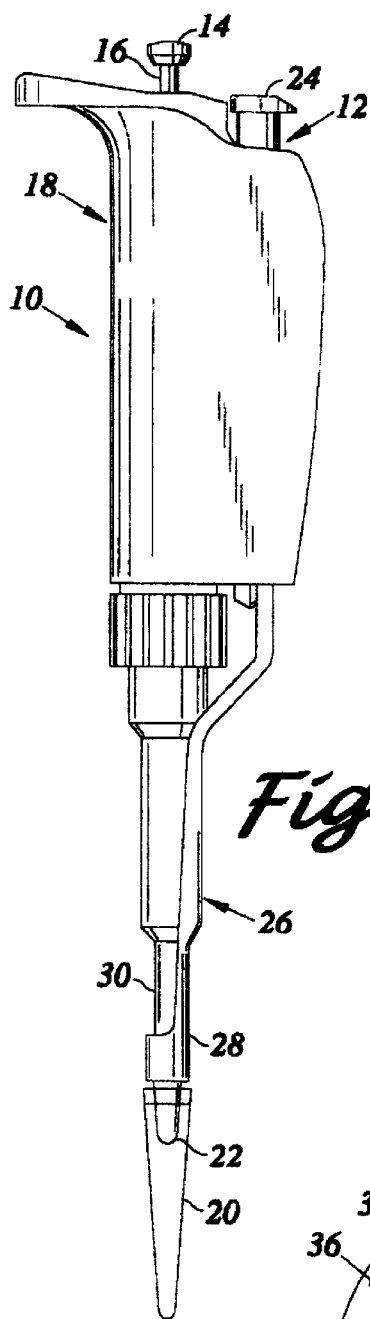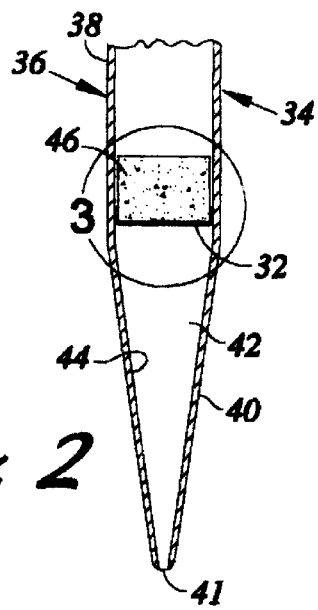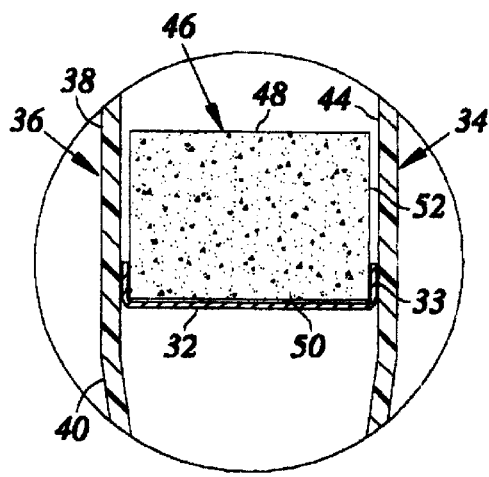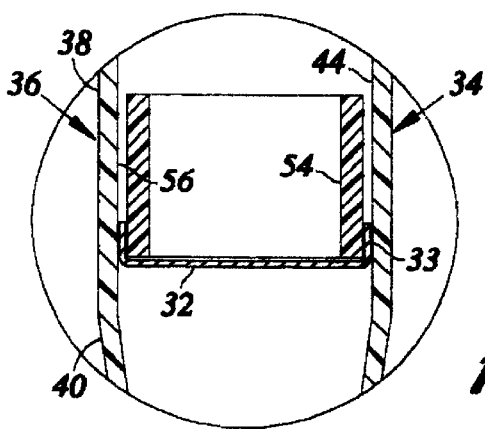

MEMBRANE FILTER PIPETTE TIP

BACKGROUND OF INVENTION

The present invention relates to improvements in disposable pipette tips and, more particularly, to an improved membrane filter pipette tip.

Use of pipette devices for the transfer and dispensing of precise quantity of fluid samples in analytical systems is well known as is the use of disposable pipette tip members for such pipettes. Disposable tips accommodate the serial use of such pipette devices in the transfer of different fluid samples without carryover or contamination.

Generally speaking, disposable pipette tips are formed of a plastic material and are of a hollow elongated tubular shape. An open proximal end of such pipette tips is designed to receive and releaseably mate with a lower end of a pipette tip mounting shaft of a pipette device while a distal end is of reduced cross section and includes a relatively small open end for passing fluids into and out of the pipette tip in response to operation of the associated pipette device.

It is often important that the fluid samples drawn into a pipette tip during aspiration operation of the associated pipette device not contact the mounting shaft or other internal components of the pipette device. To prevent such contact, it is common for disposable pipette tips to include a filter element tightly seated within the pipette tip at a location between the open proximal and distal ends of the tip. The filter member is intended to (i) freely pass air during the aspiration of fluid samples by an associated pipette device, and (ii) function as a barrier to aerosols in the fluid sample and to liquids which may be drawn into contact with the filter member as during "over pipetting".

For example U.S. Pat. No. 5,364,595 issued Nov. 15, 1994, describes a pipette including a filter member which is intended to function as a complete barrier to liquids. Unfortunately, during normal aspiration operations, such filter members have been found to function only as restricters of liquid flow and not as barriers to such flow.

U.S. Pat. No. 5,156,811 also describes a pipette tip including a filter member which is intended to function as a complete barrier to liquids. Unfortunately the type of filter material used within the filter member usually only acts as a complete barrier for a finite period of time and then allows liquid to pass therethrough. As described in the patent, the filter material is hydrophobic and includes particles of a hydrophilic material embedded in the pores of the hydrophobic filter material. Such particles sometimes dislodge from the filter material to contaminate the fluid sample during aspiration and dispensing operations of the associated pipette device. Further, if liquid sample contacts and is drawn into the pores of the filter material, such sample is often trapped within the pores of the filter material and will not dispense from the filter material during normal dispensing operation of the associated pipette. Such trapped sample is of unknown and varying quantity thereby introducing pipeting errors and nonreproducibility of pipeting results. Finally, removal of the trapped sample after the sample has contacted the filter member is difficult, time consuming and less than complete.

Accordingly, there is a continuing need for improved pipette tip including filter members which in practice allows air to freely pass therethrough while functioning as a barrier to the passage of liquids during normal fluid aspiration operation with pipette devices without trapping or contaminating any of the fluid sample.

Currently there are products known as membrane filter vents useful in medical devices which require fluids such as blood, urine, or intravenous solutions to flow in a sterile environment. Such membrane filter vents are inherently hydrophobic. They permit free passage of air while preventing the passage of aerosols and fluids such as blood, urine and intravenous solutions. When mounted in a pipette tip according to the present invention, it has been found that such membrane filter vents function as a filter material which will pass air while blocking the passage of liquids and aerosols thereby functioning as a true barrier to protect the mounting shaft and other internal components of pipette devices from contamination.

SUMMARY OF INVENTION

Basically, the present invention comprises a membrane filter pipette tip for use with a pipette device. The pipette tip includes a porous membrane secured within a hollow tube of the pipette tip such that when the pipette tip is mounted on a mounting shaft of a pipette device and the pipette device is operated in an aspiration mode to generate a maximum vacuum pressure, the porous membrane passes air but blocks the passage of liquid and aerosols carried by the air thereby protecting the mounting shaft and internal components of the pipette device from contamination. In particular, pipette devices are designed to generate a maximum vacuum pressure in aspirating fluid samples into a pipette tip mounted at a lower end of a mounting shaft of the device. In accordance with the present invention, the porous membrane is constructed in such a manner that it is hydrophobic and possesses a liquid initiation/penetration pressure that is above the maximum vacuum pressure generated by the associated pipette device during aspiration. Liquid initiation/penetration pressure is defined as the vacuum pressure required to draw liquid through the porous membrane filter.

In the improved pipette tip of the present invention, it is important that the porous membrane filter be securely seated within the pipette tip with a marginal edge thereof creating a fluid tight seal with an inner wall of the pipette tip. Preferably such mounting of the membrane filter is accomplished by a secondary filter member comprising a porous plastic plug located above the membrane filter with the membrane filter extending across and secured to a lower surface of the plug with marginal edge portions of the membrane extending upwardly along an outer surface of the plug and captured between the outer surface of the plug and an inner sidewall of the pipette tip. Thus secured, a fluid tight seal is created between the membrane and the inner sidewall of the tip and the porous plastic plug functions as a secondary or backup filter for the membrane filter (1) should the fluid seal of the membrane filter not be complete or (2) should the membrane filter have or develop an opening which allows the passage of liquid or aerosols through the membrane in response to the maximum vacuum pressure generated by the associated pipette device during aspiration operation, or, should aerosols pass with the air through the membrane filter, then preferably the porous plug is of sufficient thickness to trap and prevent the aerosols and liquid from contacting and contaminating the mounting shaft or other internal components of the pipette device to which the pipette is mounted.

BRIEF DESCRIPTION OF DRAWINGS

FIG. 1 is a side view of a standard manual pipette having a disposable pipette tip mounted on a mounting shaft adjacent a lower end of a tip ejector mechanism for the pipette.

FIG. 2 is a sectional side view of a preferred embodiment of the membrane filter pipette tip of the present invention.

FIG. 3 is an enlarged fragmentary sectional side view of a portion of the pipette tip of FIG. 2 within the circle 3.

FIG. 4 is an enlarged fragmentary side view similar to FIG. 3 showing an alternate embodiment of the filter member included within the pipette tip of the present invention.

DETAILED DESCRIPTION OF INVENTION

Figure 5:
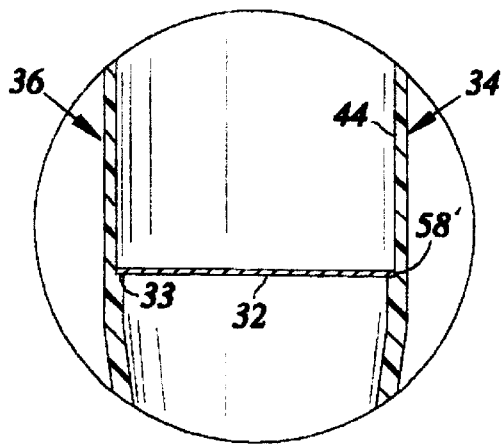
FIG. 5 is an enlarged fragmentary side view similar to FIGS. 3 and 4 of another alternate version of the filter member included in the pipette tip of the present invention.

FIG. 1 illustrates a standard manual pipette resembling the PIPETMAN pipette sold exclusively in the United States by the Rainin Instrument Co., Inc., assignee of the present invention. The manual pipette is designated in FIG. 1 by the number 10 and includes a pipette tip ejector mechanism 12 described in the U.S. Pat. No. 5,614,153, issued Mar. 25, 1997.

The pipette 10 comprises a push button 14 connected by a rod 16 to piston (not shown) located in the body or housing 18 of the pipette. The push button 14 may be depressed by a user exerting a downward force on the push button to cause downward of the piston of the pipette. Then, when the push button 14 is released, a quantity of liquid to be sampled is aspirated or sucked into a disposable tip 20 releaseably secured to a lower end of a pipette tip mounting shaft 22 of the pipette. The sample then may be dispensed or transferred into another vessel by once more exerting a downward force on the push button 14. After such use, it is common practice to eject the pipette tip 20 from the mounting shaft 22 and replace it with a new pipette tip for repeated operation of the pipette 10 in aspirating and dispensing a new sample fluid.

In aspirating the sample fluid into a lower open end of a pipette tip 20, the pipette 10 generates a maximum vacuum pressure, theoretically as high as 14.7 psi. In response to vacuum pressure, a quantity of liquid to be sampled is sucked into the pipette tip from a receptacle in which the pipette tip is immersed. As previously described, during aspiration of the liquid sample, it is usually important that the sample not contact the pipette tip mounting shaft or other internal components of the pipette 10. In the improved pipette tip of the present invention, such contact is prevented by inclusion of a porous membrane 32 within a pipette tip 34 in accordance with the present invention.

Basically, as shown in FIG. 2, the improved pipette tip 34 of the present invention comprises a hollow plastic tube 36 having a relatively large open upper end 38 for seating on a lower end of a pipette tip mounting shaft such as shaft 22 illustrated in FIG. 1 for the pipette 10. The tube 36 also includes a relatively small open lower end 40, here depicted as being frusto-conical in shape defining a relatively small opening 41 for passing fluid into and out of the pipette tip 34 upon operation of the associated pipette to which it is secured, e.g. pipette 10 of FIG. 1.

As illustrated in FIG. 2, the inside of the tube 36 is hollow and defines an open channel 42 for passing fluid from the opening 41 upward within the tube 36 in response to a vacuum pressure generated by the associated pipette device (e.g. 10 of FIG. 1) during the aspiration mode of operation of the pipette. In this regard, the open channel 42 for receiving such fluid is defined by an inner sidewall 44 of the tube 36.

By way of example only, the upper open end 38 of the tube 36 is illustrated as being generally of a cylindrical tubular shape. Alternatively, the upper end 38 may be slightly fruste-conical depending upon the shape of the pipette mounting shaft to which it is to mounted.

In the embodiment of the pipette tip 34 illustrated in FIGS. 2 and 3, the membrane filter 32 extends across the open channel 42 between the inner sidewall 44 at a location adjacent a junction of the upper end 38 and lower end 40 of the tube 36. There, the membrane filter 32 is secured against the inner sidewall 44 to form a fluid tight seal therewith. As previously described, the membrane filter 32 is porous to allow the unrestricted passage of air from the opening 41 upward through the membrane filter 32 in response to the vacuum pressure generated by the associated pipette device. However, the membrane filter is formed of a hydrophobic material and the pores size is regulated such that the membrane filter of the present invention possesses a "liquid initiation/penetration pressure" which is greater than the maximum vacuum pressure which the associated pipette device may generate during its aspiration mode of operation. The liquid initiation/penetration pressure is defined as the vacuum pressure required to draw liquid (e.g. water) upward through the membrane. Being characterized by a liquid initiation/penetration pressure which is greater than the maximum vacuum pressure which the associated pipette device is capable of generating, the membrane filter 32 insures that while air may freely travel therethrough, aerosols and liquid in the fluid sample are prevented from passing therethrough to engage the lower end of the pipette tip mounting shaft and other internal components of the pipette device to which the pipette tip 34 is mounted.

The liquid initiation/penetration pressure for a membrane filter is regulated by the hydrophobicity of the material forming the membrane and the diameter of the pores extending through the membrane. In this regard, the membrane may be formed of various materials such as polytetrafluoroethylene (PTFE) or polypropylene or polycarbonate, by way of example. All such materials are hydrophobic and may be formed to have a pore size which (1) does not allow the passage of aqueous solutions at and below the normal vacuum pressures generated by pipette devices and (2) allows air to pass through at a rate high enough that normal pipette performance is not adversely effected. Presently, PTFE appears to be the most inherently hydrophobic venting material available which achieves a high liquid initiation/penetration pressure without requiring a reduction in pore size to such a degree that air flow is significantly reduced.

Such membrane filters are obviously relatively thin and fragile. It is difficult to mount such membrane filters securely within tubes such as those associated with conventional pipette tips to create a fluid tight seal between an outer marginal edge of the membrane and the inner walls of the pipette tip. Accordingly, the present invention preferably includes structure for securely supporting the membrane filter 32 within the pipette tip 34. As illustrated in FIGS. 2, 3, 8 and 9, such supporting structure may comprise a porous plastic plug 46 mounted within the tube 36 and having an upper surface 48 facing the open upper end 38 of the tube and a lower surface 50 facing the lower open end of the tube. In addition, the plug 46 includes a side surface 52 engaging the inner sidewall 44 of the tube to form a tight friction fit for the plug 46 within the tube and to function as means for capturing a marginal edge portion 33 of the membrane filter 32 between a lower portion of the outer sidewall of the plug and the inner sidewall of the tube. Such a capturing of the outer marginal portion of the filter membrane 32 between the inner sidewall 44 and a lower portion of the side surface 52 of the plug 46 is best shown in FIG. 3.

In addition to providing structure for securing the filter membrane 32 within the tube 36 of the pipette tip 34, the porous plug 46 also functions as a secondary or backup filter for the membrane filter 32. In this regard, the plug 46 comprises a plurality of pores extending from the lower surface 50 to the upper surface 48. The material forming the porous plug 46 is hydrophobic. Having such characteristics, the porous plug 46 will restrict the flow of liquid there through while allowing air to travel freely therethrough. The porous plug also possesses sufficient depth as to prevent aerosol particles from going through the filter member. Thus, should the fluid tight seal between the marginal edge portion 33 of the membrane filter 32 and the inner sidewall 44 of the tube not be completely air tight or should there be undesired discontinuities in the material forming the membrane filter 32, the porous plug acts as a secondary or backup filter in preventing undesired passage of aerosols and liquid through the membrane filter/porous plug filter combination which otherwise might accidentally contaminate the pipette tip mounting shaft or other internal components of the pipette to which the pipette tip 34 is attached.

Figure 6:
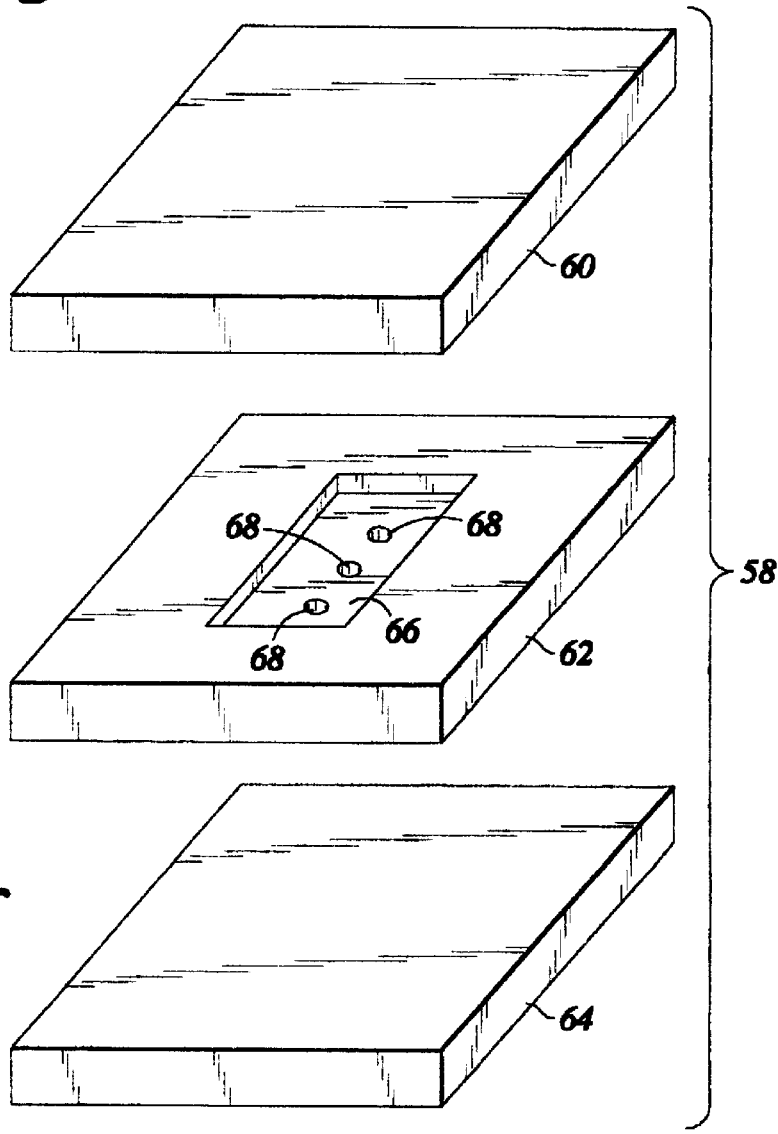
FIG. 6 is an exploded view of a mold useful in forming a composite plug/membrane filter for use in the pipette tip of the present invention.
Figure 7:
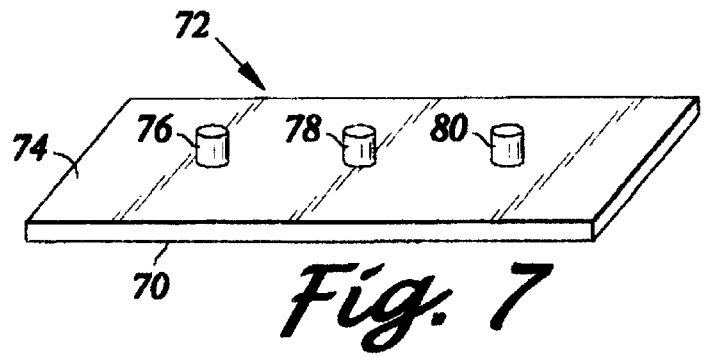
FIG. 7 is a perspective view of the composite plug/membrane piece formed using the mold of FIG. 6.
Figure 8:
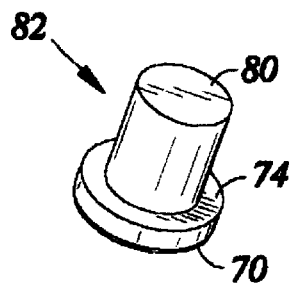
FIG. 8 is a perspective view of a composite plug/membrane filter member cut from the piece shown in FIG. 7.
Figure 9:
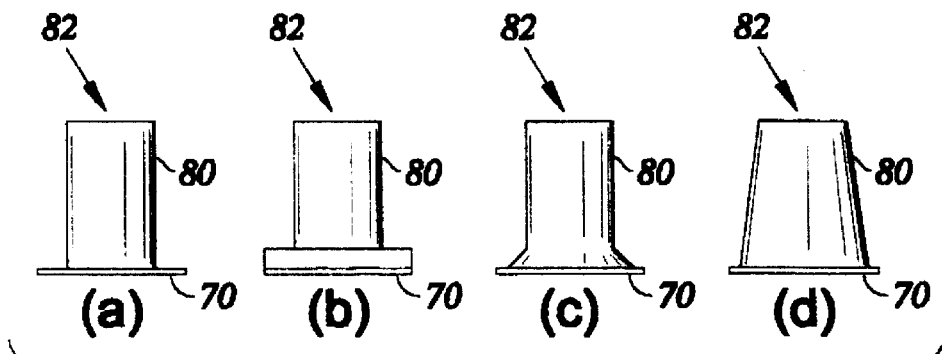
FIGS. 9(a), (b), (c) and (d) are side view of alternate forms of composite plug/membrane filter members according to the present invention.

Preferably, the membrane filter 32 and porous plug 46 comprise a composite filter member wherein the membrane filter is fused or otherwise bonded over the lower surface 50 of the porous plug with the marginal portion 33 extending there beyond. Preferably, such a composite filter member is formed using a molding process and a mold 58, a most basic form of which is depicted in the exploded view of FIG. 6. The mold 58 may consist of a upper cover plate 60, an intermediate mold plate 62 and a bottom plate 64. The mold plate 62 comprises a cavity section including a shallow generally rectangular well 66 formed in a top of the mold plate. Holes 68 are drilled through the mold plate 62 in the cavity section. In use, the mold plate 62 is placed on the solid bottom plate 64 and an ultra high molecular weight polyethylene material such as UHMWPE in powder form is poured into the through holes 68 and the well 66 filing the holes to overflowing. The material is settled by shaking and access material is scraped from the mold plate. Next, a piece of 0.5 micron pore size PTFE membrane 70 is placed over the filled cavity section covering all of the UHMWPE. Then the cover plate 60 is placed over the top of the mold plate 64 and the three plates are clamped together to complete the mold 58. The filled mold 58 then is placed in an oven preheated to about 190° C. and baked for about 30 minutes. Such heating sinters UHMWPE forming a porous solid. The heating also causes the PTFE membrane 70 to stick to the UHMWPE. After heating and cooling, the sintered part 72 as shown in FIG. 7 is moved from the mold. As shown, the parts consists of a web 74 which is formed by the well 66 with sintered plugs 76, 78 and 80 extending therefrom. The membrane 70 is fused to the surface of the web 74 as best shown in FIG. 7. After the part 72 is removed from the mold 58, individual composite plug/membrane pieces 82 such as shown in FIG. 8 may be cut from the web 74. In this regard, the membrane/web is preferably cut in a circle having a diameter larger than the diameter of the plug so that it overhangs the plug as shown in FIGS. 9(a) and (b). In FIG. 9(a) the membrane is fused to a bottom of the cylindrical plug portion to overhang an outer edge thereof. In FIG. 9(b) the membrane is fused to the lower surface of an annular pedestal at a base of the cylindrical portion of the plug. In both forms, the overhang comprises the marginal edge portion 33 which folds around the end of the plug when the composite filter piece 82 is inserted into a pipette tip as shown in FIGS. 2 and 3. As previously described, such an overhang and marginal portion 33 is preferred for proper sealing of the membrane filter to the inner sidewall 44 of the pipette tip in the preferred form of the present invention.

While the composite plug/membrane filter member shown in FIGS. 2, 3, 8, 9(a) and 9(b) comprise cylindrical plug portions, other plug shapes such as shown in FIGS. 9(c) and (d) may be utilized. In FIG. 9(c) the plug portion includes an outwardly tapered annular lower end portion formed by a counterbore in the holes 68 in the mold plate 62. In FIG. 9(d) the plug portion is frusto-conical in shape formed by a similar shaping of the mold holes 62.

Also, other structural configurations may be utilized to secure the membrane filter 32 within the tube 36 of the pipette tip 34. For example, in FIG. 4, the porous plug 46 is replaced by a plastic ring or sleeve 54 dimensioned to fit tightly downward within the tube 36 and to capture the marginal edge portion 33 of the membrane filter 32 between a lower portion of an outer annular surface 56 of the sleeve and inner surface 44 of the tube. Thus secured, the membrane filter 32 functions as previously described in blocking the passage of aerosols and liquids upward within the pipette tip 34 to contact the pipette tip mounting shaft or other internal components of the pipette tip device to which the pipette tip is mounted.

A different the structure for supporting the membrane filter 32 within the tube 36 of the pipette tip 34 is shown in FIG. 5 and comprises an annular shoulder 58' formed in the inner sidewall 44 of the tube 36. The outer marginal portion 33 of the membrane filter 32 rests on and is secured to the shoulder 58' as by heat sealing or ultrasonic welding in a conventional manner. Thus secured within the tube 36, the membrane filter 32 of FIG. 5 functions to allow air to freely pass therethrough during aspirating operation of the associated pipette device while blocking passage of aerosols and liquid which might otherwise contaminate the inner components of the pipette device.

In the foregoing, various embodiments of the improved pipette tip of the present invention have been described. It should be appreciated from such description that modifications may be made in the specific embodiments without departing from the spirit of the present invention which is to be limited in scope only by the terms of the following claims.

What is claimed is:

1. A membrane filter pipette tip comprising:

a hollow tube having a relatively large open upper end for seating on a lower end of a pipette tip mounting shaft of a pipette device and a relatively small open lower end for passing fluid into the lower end of the tube upon operation of the pipette device, and an open channel between the upper and lower ends of the tube;

a porous membrane within the open channel; and support structure comprising a porous plug extending across the channel within the tube and including an upper surface facing the open end of the tube, a lower surface facing the open lower end of the tube and a sidewall engaging an inner surface of the tube and supporting the porous membrane to extend over the lower surface of the plug across the open channel with a marginal edge of the porous membrane secured against an inner surface of the tube by a marginal edge portion of the membrane surrounding a lower portion of an outer sidewall of the plug and being captured between the outer sidewall of the plug and the inner sidewall of the tube.

2. A pipette-pipette tip combination, comprising:

a pipette housing;

a pipette tip mounting shaft extending from the pipette housing;

a hollow pipette tip mounted on the mounting shaft;

a piston rod for moving within the pipette housing to (1) generate a maximum vacuum pressure within the pipette tip to draw a fluid sample into the pipette tip and (2) then dispense the sample from the pipette tip; and a porous membrane supported by support structure within the pipette tip with a marginal edge of the membrane secured against an inner sidewall of the tip for passing air drawn by the vacuum pressure from an end the pipette tip through the membrane and having a liquid initiation-penetration pressure greater than the maximum vacuum pressure whereby any liquid in the fluid sample is prevented from passing through the membrane, the porous membrane being formed by a hydrophobic material and secured within the pipette tip by a backup filter comprising a porous plastic plug and the membrane extending over a lower surface of the plug with a marginal edge portion of the membrane surrounding a lower portion of an outer sidewall of the porous plug and being captured between the outer sidewall of the plug and an inner sidewall of the pipette tip.

* * * * *